US006946258B2

(12) United States Patent
Padhye et al.

(10) Patent No.: US 6,946,258 B2
(45) Date of Patent: Sep. 20, 2005

(54) RAPID, IMMUNOCHEMICAL PROCESS FOR MEASURING THIOPURINE METHYLTRANSFERASE

(75) Inventors: Nisha V. Padhye, Lincoln, NE (US); Andre' Quintanar, Santa Clara, CA (US); R. Michael Nelson, Lincoln, NE (US)

(73) Assignee: Biologix Diagnostics, LLC, Shawnee Mission, KS (US)

( * ) Notice: Subject to any disclaimer, the term of this patent is extended or adjusted under 35 U.S.C. 154(b) by 0 days.

(21) Appl. No.: 10/090,918

(22) Filed: Mar. 4, 2002

(65) Prior Publication Data

US 2003/0170764 A1 Sep. 11, 2003

(51) Int. Cl.[7] ............................................. G01N 33/573
(52) U.S. Cl. ...................... 435/7.4; 435/7.1; 435/7.92; 435/7.15; 436/517
(58) Field of Search .................. 435/7.4, 7.1, 7.92, 435/15; 436/517

(56) References Cited

U.S. PATENT DOCUMENTS

| | | | |
|---|---|---|---|
| 5,120,753 A | | 6/1992 | MacLeod |
| 5,169,756 A | * | 12/1992 | Ranby et al. ................. 435/7.4 |
| 5,231,108 A | | 7/1993 | MacLeod |
| 5,470,737 A | | 11/1995 | Weinshilboum et al. |
| 5,733,915 A | | 3/1998 | Sandborn |
| 5,856,095 A | | 1/1999 | Evans et al. |
| 5,905,081 A | | 5/1999 | Sandborn |
| 6,166,024 A | | 12/2000 | Sandborn |
| 2001/0006970 A1 | | 7/2001 | Seidman et al. |
| 2002/0028476 A1 | * | 3/2002 | Barstad ....................... 435/15 |

FOREIGN PATENT DOCUMENTS

WO    WO 97/07201    2/1997

OTHER PUBLICATIONS

Kroplin et al, Thiopurine S–Methyltransferase activity in human erythrocytes: a new HPLC method using 6–thioguanine as substrate, European Journal of Clinical Pharmacology (1998), vol. 54, pp. 265–271.*

Micheli et al, Thiopurine methyltransferase activity in the erythrocytes of adults and children: an HPLC–linked assay, Clinica chimica Acta, (1997) vol. 259, pp. 161–168.*

Pressman et al.; "The Serological Properties of Simple Substances. IV. Hapten Inhibition of Precipitation of Antibodies and Polyhaptenic Simple Substances"; Hapten Inhibition of Precipitation of Antibodies and Polyhaptens; Jam. Chem. Soc. vol. 64—pp. 3015–3020 (1942).

K. Landsteiner, M.D., and J. Van Der Scheer; "Serological Studies on Azoproteins"; (From the Laboratories of The Rockefeller Institute for Medical Research); J. Exp. Medicine vol. 59—pp. 751–768 (1934).

* cited by examiner

*Primary Examiner*—Long V. Le
(74) *Attorney, Agent, or Firm*—McKee, Voorhees & Sease, P.L.C.

(57) ABSTRACT

The present invention relates to non-isotopic immunoassays for thiopurine methyltransferase (TPMT). The immunoassays of this invention may be homogenous or heterogenous, in which detection of the TPMT-catalyzed reaction product relies upon specific binding of antibody to 6-MMP or other TPMT-catalyzed reaction products. Preferred embodiments of this invention include a Rapid Immunomigration Cassette and an assay carried out in ELISA assay format.

9 Claims, 2 Drawing Sheets

RAPID, IMMUNOCHEMICAL PROCESS FOR MEASURING THIOPURINE METHYLTRANSFERASE

FIELD OF INVENTION

The present invention relates to rapid immunoassays for thiopurine methyltransferase. Specifically, the invention relates to immunoassays that use antibody specific for the methylated reaction product of a TPMT-catalyzed enzyme reaction.

BACKGROUND OF THE INVENTION

Thiopurine Methyltransferase (TPMT; EC 2.1.1.67) is a cytoplasmic enzyme that catalyzes the S-methylation of aromatic and heterocyclic sulfhydryl compounds (Ames et al., 1986; Weinshilboum, 1989; Deininger et al., 1994). S-adenosylmethionine (SAM) is the methyl donor in this Mtase catalyzed reaction, and S-adenosylhomocysteine (SAH) and 6-methylmercaptopurine are released as reaction products.

TPMT is the enzyme responsible for metabolizing several anti-cancer thiopurine drugs, including thioguanine, azathioprine, and mercaptopurine, through the addition of a methyl group to the sulfhydryl group of these drugs. Methylation prevents the incorporation of the drugs into extending nucleic acid polymers, limiting the drugs' potency. Consequently, the dosage of the drug delivered to a patient must exceed the patient's ability to inactivate the drug. As there are numerous polymorphisms of TPMT possessing disparate levels of activity, it is important to tailor the drug dosage to the patient.

TPMT activity exhibits genetic polymorphism in the human population. About ~89% of Caucasians and African Americans have high TPMT activity (wild type), ~11% show intermediate activity (presumed heterozygotes), and ~1 in 300 (homozygotes) display complete TPMT deficiency, which is inherited as an autosomal recessive trait (Weinshilboum, 1980; Weinshilboum et al, 1999). Such frequent mutations which occur in over 1% of the population are formally termed polymorphisms (Meyer et al, 1990; Iyer and Ratain, 1998). As a result of these genetic polymorphisms, a significant fraction of the population cannot metabolize certain commonly employed therapeutic drugs. For example, in TPMT-deficient patients, 6-mercaptopurine cannot be methylated to 6-methylmercaptopurine.

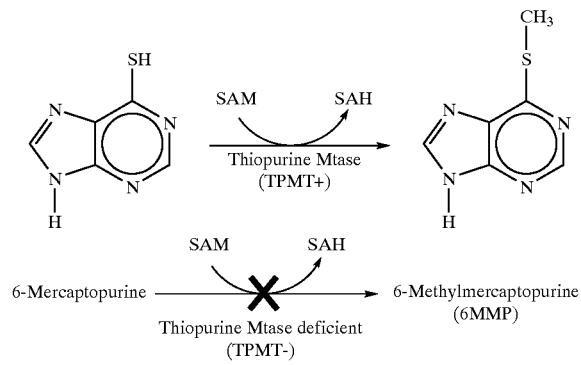

The methylated reaction product, 6-methylmercaptopurine (6-MMP), is normally metabolized in the liver. However, unmethylated 6-mercaptopurine builds up to toxic levels in the bloodstream in TPMT-deficient individuals. As a part of multiagent chemotherapy for the treatment of acute lymphoblastic leukemia, 6-mercaptopurine (or 6-thioguanine) is typically used in large doses over an extended time period. Mercaptopurine is a prodrug with no intrinsic anticancer activity, requiring intracellular conversion to 6-thioguanine nucleotides. These metabolites, in turn, are incorporated into DNA, as one mechanism of its antiproliferative effects (Lennard et al, 1987; Elion, 1989).

Patients with low levels of TPMT activity accumulate significantly higher levels of thioguanine nucleotides when treated with standard mercaptopurine dosages, leading to severe hematopoietic toxicity. On the other hand, "standard" doses of these drugs may undertreat patients with high levels of enzyme activity (Lennard et al, 1990). Due to TPMT deficiency, about one in ten childhood leukemia patients cannot tolerate the high doses of thiopurines which are used in the normal chemotherapeutic regimen (Lennard et al, 1987; Lennard et al, 1993). Similar problems are encountered in certain dermatology patients (Jackson et al, 1997), patients with Crohn's Disease (Sandborn et al, 1995), or organ transplant recipients (Schutz et al, 1996) when they are treated with thiopurine drugs.

The most common strategy for thiopurine administration is to give all patients low doses of 6-mercaptopurine or azathioprine; and to then gradually increase the dose (Weinshilboum, 1984; Evans et al, 1991). At certain dosages, one in ten patients will become ill. Lower doses of thiopurines and/or alternative therapy are then given to TPMT-intolerant patients. Obviously, this course of action is less than ideal since 90% of patients receive unaggressive treatment; and the remaining 10% are poisoned by their 'therapy' (Lennard and Lilleyman, 1987; Lennard et al, 1993).

TPMT-deficient patients suffer greatly when given thiopurine drugs. Not only do children with leukemia suffer from a life-threatening cancer, but the consequences of their chemotherapy can actually be worse than their disease (Lennard et al, 1987). Some TPMT-deficient patients die from acute thiopurine toxicity (Schutz et al, 1993).

A more rational therapeutic approach for thiopurine therapy strategy would be to first measure TPMT enzyme activity in patients who are candidates for thiopurine drugs, and then adjust the thiopurine dosage on an individual basis (Lennard et al., 1987; Lennard and Lilleyman, 1996; Jackson et al., 1997; Krynetski and Evans, 1998; Lennard, 1998; Lennard, 1999).

TPMT activity is typically measured from lysed red blood cells. Enzyme activity in red blood cell lysates corresponds to the level of TPMT in human liver, kidney, and normal lymphocytes. Currently used methods for measuring erythrocyte TPMT activity rely on the transfer of methyl groups from $^{14}$C-methyl-SAM to 6-mercaptopurine, extraction of the radiolabeled $^{14}$C-methylated reaction product into 20% isoamyl alcohol: 80% toluene, followed by liquid scintillation counting (Weinshilboum et al., 1978; University of Rochester, 1999). The total time needed to carry out this 8-step TPMT assay procedure is >3 hours, requires the use of $^{14}$C-radiolabeled SAM, involves the disposal of toxic organic waste, and costs over $100/assay (University of Rochester, 1999). At the present time, radioenzymatic TPMT assays are necessarily carried out in laboratories which are licensed and equipped for the handling of radioisotopes, such as hospital nuclear medicine laboratories and university medical genetics departments.

Non-isotopic TPMT assays based upon HPLC chromatography have been described (Boulieu and Lenoir, 1995; Kroplin et al., 1996; Micheli et al., 1997). However, these labor-intensive assays require extensive liquid handling and sample processing. Further, such heterogeneous Mtase assays are not suitable for routine point-of-care diagnosis.

Alternatively, DNA-based tests have been developed for common TPMT allelic variants (Krynetski et al., 1995; Szumlanski et al., 1996; Yates et al., 1997; Evans and Krynetski, 1999; Krynetski et al., 1999). Unfortunately, such genotypic tests have three major limitations: (i) DNA-based tests cannot detect any new or uncharacterized allelic variants; (ii) genotypic tests do not allow the clinician to determine what dose of thiopurine drugs, if any, should be given to a particular patient; and (iii) rapid DNA-based tests are relatively expensive. For example, the DNA Chip-based technology for TPMT detection developed by Nanogen (San Diego, Calif.) relies upon an instrument which costs over $175,000; and each DNA Chip costs approximately $200 (Heller, 2000). While elegant in principle, such high cost devices and reagents are generally not affordable. Even the designers of DNA-based tests for TPMT deficiency admit that a phenotypic test for blood or tissue enzyme activity would be preferable (Krynetski et al., 1995; Spire-Vayron de la Moureyre et al., 1998).

The development of rapid homogenous assays for TPMT would be technically advantageous, especially if the assays could be carried out without the need for radioisotopes. The cost and environmental hazard of radioenzymatic assays would be reduced, while the speed and technical simplicity of Mtase assays would be improved.

It is therefore a primary objective of the present invention to provide a method and means of providing an improved phenotypic assay to detect DNA sequence alterations in the human TPMT gene.

It is a further objective of the present invention to provide a method and means of detecting TPMT enzyme levels that is less labor intensive, time-consuming, and expensive than conventional assays.

It is a further objective of the present invention to provide a method and means of measuring TPMT that is both qualitative and quantitative.

It is yet a further objective of the present invention to provide an immunochemical method for detecting the methylated product of TPMT-catalyzed reactions.

It is still a further objective of the present invention to provide a method and means of detecting TPMT enzyme activity that allows the clinician to determine what dose of thiopurine drugs, if any, should be given to a particular patient.

These and other objectives will become clear from the following detailed description of the invention.

SUMMARY OF THE INVENTION

The present invention relates to a method and means for the rapid detection and determination of thiopurine methyltransferase (TPMT) in a biological sample. More specifically, the invention relates to immunochemical immunoassays for the detection of TMPT that are antibody specific for 6-methylmercaptopurine (6-MMP), the reaction product of TPMT-catalyzed in vitro methylation of 6-mercaptopurine, or any other methylated reaction product of a TPMT-catalyzed enzyme reaction product.

The immunoassays of this invention first involve the isolation of a biological sample suspected of containing TPMT. This sample may be a red blood cell lysate, serum, saliva, or tissue extract. After in vitro methylation of a suitable substrate (such as 6-mercaptopurine) in the presence of S-adenosyl-methionine, the biological sample is then reacted with at least one antibody to the methylated reaction product of a TPMT-catalyzed enzymatic reaction. Finally, the antibodies bound to the antigen, if any, are detected, thereby indicating the presence of TPMT.

The present invention further relates to a kit for the detection of TPMT which comprises, (a) a substrate with at least one identifying antigen to TPMT bound on a surface of the substrate; (b) antibody to the methylated reaction product of a TPMT catalyzed enzyme reaction product; and (c) at least one reagent for detection of an antibody in a biological fluid, and which said antibody binds to the antigen of TPMT.

The rapid assays for of this invention are technically advantageous in comparison to previous TPMT assays. First, they may be carried out without the need for radioisotopes. Further, the immunoassays of the present invention reduce the cost and environmental hazard associated with conventional radioenzymatic assays, while improving the speed and technical simplicity of the TPMT assay. Moreover, the TPMT immunoassays of this invention can provide both qualitative and quantitative detection of TPMT.

Over 10% of the world population are deficient in TPMT, and many of these >600 million individuals will receive thiopurine drugs, such as 6-mercaptopurine or azathioprine to treat a variety of medical conditions including leukemia, organ transplantation, dermatological conditions, autoimmune hepatitis, and inflammatory bowel disease. For these reasons, the rapid, immunochemical assays for TPMT in accordance with this invention will have a significant social and economic impact, and allow for safer implementation of TPMT drug therapy.

DETAILED DESCRIPTION OF THE INVENTION

Figure 1:
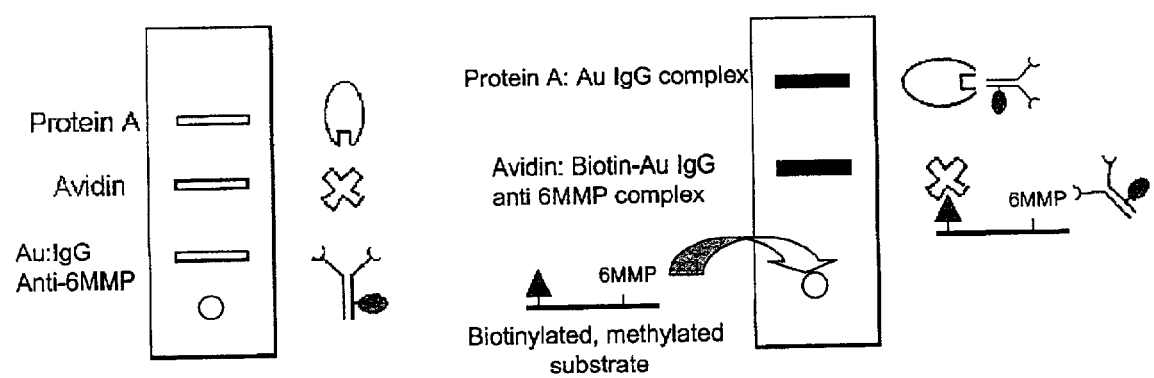
FIG. 1 is a schematic diagram of a preferred Rapid Immunomigration (RIM) cassette for TPMT in accordance with this invention. As shown, a biotinylated 6-MP substrate is methylated in vitro using TPMT in the presence of SAM as a methyl donor. The biotinylated reaction product, a conjugate covalently attached to 6-MMP, is squired into the sample well of an RIM cassette containing dried gold-labeled anti-6-MMP IgG, Avidin, and Protein A. The aqueous sample migrates up the paper in the cassette, and visible purple immunoprecipitates are visible after about 5 minutes. The lower purple band (Avidin: biotin-6-MMP: Au-Anti-6-MMP IgG complex) indicates the presence of 6-MMP methylated reaction product of TPMT-catalyzed methylation of 6-MP. The upper purple band (Protein A: Au-Anti-6-MMP IgG complex) serves as an internal control to verify that the reagents in the cassette are functioning properly.

The present invention relates to rapid immunoassays for TPMT, using antibody specific for the riboside of 6-methylmercaptopurine (6-MMP), or any other methylated reaction product of a TPMT-catalyzed enzyme reaction product. These non-isotopic immunoassays will allow rational drug therapy to be implemented using inexpensive, point-of-care diagnosis.

As used herein, the term "biological sample" refers to any sample suspected of containing TPMT. The sample is typically an aqueous solution such as a body fluid from a host, for example, urine, whole blood, plasma, serum, saliva, semen, stool, sputum, cerebral spinal fluid, tears, mucus, or the like, but preferably is blood. The sample can be pretreated and can be prepared in any convenient medium that does not interfere with the assay. An aqueous medium is preferred.

As used herein, the term "conjugate" refers to a compound comprised of two or more molecules bound together, optionally through a linking group, to form a single structure. The binding can be made by a direct connection (e.g. a chemical bond) between the molecules or by use of a linking group.

As used herein, the term "hapten" refers to a compound capable of binding specifically to corresponding antibodies, but do not themselves act as immunogens (or antigens) for preparation of the antibodies. Antibodies which recognize a hapten can be prepared against compounds comprised of the hapten linked to an immunogenic (or antigenic) carrier.

As used herein, the term "immunogenic carrier" refers to a group which, when conjugated to a hapten and injected into a mammal, will induce an immune response and elicit the production of antibodies that bind to the hapten, in this case MPA. Immunogenic carriers are also referred to as antigenic carriers. Typical immunogenic carriers include, without limitation, poly(amino acids), polysaccharides, nucleic acids and particles. Other suitable immunogenic carriers include albumins, serum proteins, e.g., globulins, ocular lens proteins and lipoproteins. Illustrative proteins include bovine serum albumin, keyhole limpet hemocyanin, egg ovalbumin, and bovine gammaglobulin.

As used herein, the term "support" or "surface" refers to a solid phase which is a porous or non-porous water insoluble material that can have any one of a number of shapes, such as strip, rod, particle or beads.

As used herein, the term "label" or "labels" include, but are not limited to, enzymes such as alkaline phosphatase, glucose-6-phosphate dehydrogenase, and horseradish peroxidase, ribozyme, a substrate for a replicase such as QB replicase, promoters, dyes, fluorescers, such as fluorescein, isothiocynate, rhodamine compounds, phycoerythrin, phycocyanin, allophycocyanin, o-phthaldehyde, and fluorescamine, chemiluminescers such as isoluminol, sensitizers, coenzymes, enzyme substrates, radiolabels, particles such as latex or carbon particles, liposomes, cells, etc. which may be further labeled with a dye, catalyst or other detectable group.

As used herein, the term "receptor" and "receptor protein" are used herein to indicate a biologically active proteinaceous molecule that specifically binds to (or with) other molecules.

As used herein, the term "ligand" refers to a molecule that contains a structural portion that is bound by specific interaction with a particular receptor protein.

As used herein, the term "antibody" refers to immunoglobulin molecules and immunologically active portions of immunoglobulin molecules, i.e., molecules that contain an antibody combining site or paratope.

As used here, the terms "monoclonal antibody" or "monoclonal antibody composition" refer to an antibody molecule that contains only one species of antibody combining site capable of immunoreacting with a particular antigen. A monoclonal antibody composition thus typically displays a single binding affinity for any antigen with which it immunoreacts. A monoclonal antibody composition is typically composed of antibodies produced by clones of a single cell called a hybridoma that secretes (produces) only one type of antibody molecule. The hybridoma cell is formed by fusing an antibody-producing cell and a myeloma or other self-perpetuating cell line. Such antibodies were first described by Kohler and Milstein, *Nature* 256:495–497 (1975), the disclosure of which is herein incorporated by reference. An exemplary hybridoma technology is described by Niman et al., *Proc. Natl. Acad. Sci. U.S.A.*, 80:4949–4953 (1983). Other methods of producing a monoclonal antibody, a hybridoma cell, or a hybridoma cell culture are also well known. See e.g., *Antibodies: A Laboratory Manual*, Harlow et al., Cold Spring Harbor Laboratory, 1988; or the method of isolating monoclonal antibodies from an immunological repertoise as described by Sasatry, et al, Proc. *Natl. Acad. Sci. USA*, 86:5728–5732 (1989); and Huse et al., *Science*, 246:1275–1281 (1981). The references cited are hereby incorporated herein by reference.

Immunodiagnostics using specific antibodies is practical because of the sensitivity, specificity, speed, reliability and simplicity of these assays. Antibodies to modified nucleosides were first described in the 1960's (Erlanger and Beiser, 1964; Stollar, 1980), but have not gained wide popularity because of the practical difficulty in preparing high titer antibodies to 5-methylcytidine ($^{5m}$C).

A first step towards developing a rapid, immunochemical assay for TPMT involves obtaining adequate quantities of the human TPMT enzyme for control assays. This is preferably accomplished by cloning and overexpressing the TPMT enzyme from human lymphocyte DNA, based upon the sequence data of Szumlanski et al. (1996), the disclosure of which is hereby incorporated by reference.

Briefly, a preferred cloning strategy for use in this invention is to insert the PCR-amplified TPMT gene fused in-frame to the N-terminus of the LacZ gene in the plasmid cloning vector pGEM-3Zf(+)(Promega, Madison, Wis.). A 738 base pair DNA fragment containing the human TPMT gene is PCR-amplified, digested using BamHI and HindIII, then inserted between the BamHI site and the HindIII site of pGEM-3Zf(+). Persons skilled in the art can readily ascertain other methods for obtaining human TPMT enzyme for use in control assays in accordance with this invention.

A further step in producing the assays of this invention is to produce suitable anti-6-MMP antibodies or antibodies to a methylated reaction product of a TPMT-catalyzed enzyme reaction product. These antibodies are used to immunochemically detect 6-MMP, the reaction product of TPMT-catalyzed methylation of 6-mercaptopurine, or other methylated reaction products of TPMT. As noted above, the antibodies of this invention may be monoclonal antibodies that contain only one species of antibody combining site capable of immunoreacting with a particular antigen Generally, immunogens are prepared by attaching the individual antigenic molecule onto an immunogenic carrier molecule capable of inducing antibody synthesis in animals.

An immunogen is defined herein as a substance of sufficient size that when introduced into an animal stimulates the production of antibodies reactive with the specific antigen or epitope. Immunogenic carrier is defined herein as a protein or other high molecular weight compound to which an antigen or epitope is conjugated in vitro and which renders the antigen or epitope capable of stimulating or increasing an immune response. The antigens of the present invention may be synthesized using any suitable synthesis technique. Such procedures are well known to persons skilled in the art.

A preferred method for synthesizing the antibodies of this invention uses an adaptation of the periodate oxidation method of Erlanger and Beiser (1964), as modified by Stollar (1980). In summary, 6-methylmercaptopurine riboside is oxidized to the dialdehyde. The resulting dialdehyde is then mixed with a carrier protein to form Schiff's bases to the free amino groups of lysine. The polyclonal antibodies are then produced using a 6-MMP riboside conjugate for injection into an appropriate animal (i.e. goat, sheep, rabbit or the like), followed by subsequent boosts. Serum samples are collected following each booster injection. The anti-6MMP IgG is purified using conventional methods, such as preparative ion exchange or affinity chromatography on Staph A Sepharose, techniques well known in the art.

The antigens are covalently coupled to high molecular weight carrier proteins which include, but are not limited to, bovine serum albumin (BSA), bovine thyroglobulin (BT), keyhole limpet hemocyanin (KLH), ovalbumin (OA), and the like, with BSA and BT being preferred. The oxidized ribosides containing methylated purine derivatives are coupled to the linking amino acid, lysine, followed by borohydride reduction.

Monoclonal antibodies of the present invention can be produced using conventional methods, including by initiation of a monoclonal hybridoma culture comprising a nutrient medium containing a hybridoma that produces and secretes antibody molecules of the appropriate polypeptide specificity. The culture is maintained under conditions and for a time period sufficient for the hybridoma to secrete the antibody molecules into the medium. The antibody-containing medium is then collected. The antibody-containing medium can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/1 glucose, 20 mm glutamine, and 20% fetal calf serum. An exemplary inbred mouse strain is the BALB/c.

The assays of this invention can be performed either without separation (homogeneous) or with separation (heterogeneous) of any of the assay components or products. It is preferred that the assays are homogeneous. Homogeneous immunoassays are exemplified by enzyme multiplied immunoassay techniques ("EMIT") disclosed in Rubenstein, et al., U.S. Pat. No. 3,817,837; immunofluorescence methods such as those disclosed in Ullman, et al., U.S. Pat. No. 3,996,345; enzyme channeling techniques such as those disclosed in Maggio, et al., U.S. Pat. No. 4,233,402; and other enzyme immunoassays such as the enzyme linked immunosorbant assay ("ELISA") are discussed in Maggio, E. T. supra. Exemplary of heterogeneous assays are the radioimmunoassay, disclosed in Yalow, et al., J. Clin. Invest. 39:1157 (1960). The above disclosures are all incorporated herein by reference. For purposes of this invention, ELISA assays are preferred.

The assays of this invention are used to determine the reactivity of anti-6-MMP IgG (or other methylated TPMT reaction product IgG), and its cross-reactivity, if any to 6-MP (TPMT substrate). Specifically, the assays determine whether TPMT enzyme can methylate 6-MP bound to carrier protein, and if the anti-6-MMP antibody can detect the methylated 6-MMP reaction product, without reacting with 6-mercaptopurine.

Thus, in preferred embodiments of this invention, the antibody or antigen reagent component can be affixed to a solid matrix to form a solid support that is separately packaged in the subject diagnostic systems. The reagent is typically affixed to the solid matrix by adsorption from an aqueous medium, although other modes of affixation, well known to those skilled in the art, can be used. Useful solid matrices are well known in the art. Such materials include the cross-linked dextran available under the trademark SEPHADEX from Pharmacia Fine Chemicals (Piscataway, N.J.); agarose; polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry powder, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

The present invention also contemplates any method that results in detecting TPMT. The method for detecting TPMT comprises the formation of an immunoreaction product between TPMT and an anti-TPMT antibody molecule, as disclosed herein, and the subsequent detection of the immunoreaction product so formed. The TPMT to be detected can be present in a biological or vascular fluid sample, such as a blood sample, or can be present in a body tissue. Those skilled in the art will understand that there are numerous well known clinical diagnostic chemistry procedures that can be utilized to form detectable immunocomplexes. Thus, while exemplary assay methods are described herein, the invention is not so limited.

Various heterogeneous and homogeneous assay protocols can be employed, either competitive or non-competitive for detecting the presence and preferably amount of TPMT in a body sample, preferably a body fluid sample, more preferably a vascular fluid sample such as blood. The method involves the admixture of a blood sample with antibody molecules that immunoreact with TPMT but not with unbound molecules. The TPMT can be detected or measured using any type of assay, such as enzyme-linked immunosorbent assay, radioimmunoassay, radial immunodiffusion assay (RID), or Western blotting assay. Such assays are well known to persons skilled in the art.

Biological assay conditions are those that maintain the biological activity of the antibody molecules and polypeptide molecules of this invention and the TPMT sought to be assayed. Those conditions include a temperature range of about 4–45° C. at a pH value of 5–9, and an ionic strength varying from that of distilled water to that of about one molar sodium chloride, preferably about that of physiological saline.

The present invention includes two preferred rapid immunoassays for non-isotopic detection of TPMT in lysed red blood cell lysates: (1) rapid immunimigration (RIM) cassette assay; and (2) quantitative ELISA assay for red blood cell TPMT. Both of these immunoassays rely upon the use of purified anti-6-MMP, the reaction product of TPMT-catalyzed in vitro methylation of 6-mercaptopurine.

First, RIM cassette assays have been developed. These inexpensive cassettes allow for rapid, homogenous TPMT immunoassays. A purple band in the lower mobility position of the cassette signifies the presence of wild-type levels of TPMT, while a light purple or absent band indicates partial or complete TPMT deficiency.

Immunochromatography, also known as Rapid Immunomigration (RIM) is one of the fastest and most practical techniques for detecting antibody-antigen interactions. In the most common format of this method, an antibody specific to a given antigen is fixed to colloidal gold molecules, which is dried as a stripe on chromatography paper (usually a nitrocellulose or PVDF) strip encased in a plastic holder or "immunocassette". An additional "capture" molecule, such as avidin or a gold/IgG complex (Protein A) is also dried onto the paper. Other appropriate immunocapture molecules may be readily ascertained by those skilled in the art. Gold-labeled antibodies and/or avidin bind to haptens which are introduced into the immunocassette.

A drop (about 10–12 µl) of the substance to be tested is dropped through a window in the plastic holder or immunocassette onto the paper within. In positive (immunoreactive) samples, an antigen-antibody-gold particle complex is formed. This complex migrates along the paper and is eventually trapped by a ligand that is coated to the paper at a specific location. This trapping ligand may be Protein A, an antibody specific for the primary antibody, and/or avidin, which is capable of trapping the biotinylated gold-antibody-antigen complexes. Trapping of the immunoprecipitate complex allows for visualization of the particles in a transparent window in the RIM apparatus.

In the RIM cassettes of this invention, 6-MP bound to a carrier protein is methylated in vitro in the presence of S-adenosylmethionine using red blood cell lysate. (See FIG. 1). After a time period sufficient to complete the methylation, the reaction product is placed in the sample well of an immunocassette containing labeled anti-6-MMP IgG and protein dried onto the membrane. Using such immunocassettes, a visible purple color appears in the lower window of the immunocassette when immunoreactive molecules are present in the sample (i.e., TPMT +/+, thus indicating that thiopurine drugs may be safely administered. The intensity of the color also allows semi-quantitation. For example, a dark purple line indicates TPMT +/+ while a light purple line indicates TPMT +/–. On the other hand, if no methylated immunoreactive molecules are present, the immunocassette will remain colorless. This phenotypic test will allow physicians and pharmacologists to rapidly identify the approximately 90% of patients who can tolerate thiopurine drugs.

The immunocassettes of this invention are also intended to include an internal control to allow the user to validate that the cassette reagents (i.e. Au-labeled antibody, avidin, Protein A, etc.) are working as expected. The migration position of the internal control is arranged to be slightly different from that of the experimental sample.

A second preferred embodiment of this invention includes quantitative ELISA assay for red blood cell TPMT. In certain cases, especially those in which TPMT levels are low or absent using rapid immunocassette assays, it may be important to more precisely determine the levels or TPMT activity. A quantitative ELISA assay will help physicians in determining the correct dosage of thiopurine drugs which should be given to patients.

"ELISA" refers to an enzyme-linked immunoabsorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4$^{th}$ Edition of *Basic and Clinical Immunology* by D.P. Sites et al., published by Lange Medical Publications of Los Altos, Calif. In 1982 and in U.S. Pat. Nos. 3,654,090; 3,850,752; and 4,016,043, the disclosures of which are herein incorporated by reference.

ELISA is more labor-intensive than the RIM cassette of this invention described above, and is not a homogenous assay. However, the ELISA is quantitative: absorbance at 450 nm allows the amount of 6-MMP formed in TPMT-catalyzed reactions to be measured.

Like the RIM immunocassette assay of this invention, the ELISA test relies on the use of anti-6-MMP antibodies. Quantitative ELISA tests are performed using 1–20 units of purified TPMT enzyme added per well. Absorbance at about 450 nm is then measured and plotted against units/ml of TPMT activity. The assay is repeated at least three times and mean values are used to generate a standard plot. Since it has already been shown that enzyme activity is a linear function of concentration, the plot will correspond absorbance to units of enzyme from the standard plot. After the TPMT ELISA test is calibrated using purified enzyme as a positive control, the amount of TPMT enzyme activity in red blood cell lysates is then measured. It is possible to automate this assay for a large hospital diagnostic lab where hundreds of samples need to be tested.

Generally, the ELISA assays of this invention first involve the preparation of 6MP-carrier protein substrate, as already described above. Wells of plastic ELISA strips are then coated with 6MP-carrier protein, preferably at a concentration of 50–100 µg/ml 6MP-carrier protein. If present, the TPMT in the biological sample added to the ELISA wells catalyzes S-methylation of 6-MP to 6-MMP, or other TPMT reaction product. Anti-6-MMP IgG then covalently binds to the 6-MMP reaction product, and peroxidase conjugated protein binds to the IgG. The peroxidase conjugated protein is preferably horseradish peroxidase (HRP) labeled Protein A, but other peroxidase conjugated proteins are also appropriate for use in this invention, including but not limited to, goat anti-rabbit IgG, sheep anti-rabbit IgG, etc. The 6-MMP reaction becomes colored in the presence of a peroxidase substrate, such as tetramethylbenzidine (TMB). Other appropriate peroxidase substrates include 2,2'-azinodi-(3- ethylbenzthiazoline-6-sulfonate)(ABTS) and ortho-phenylenediamine (OPD). The optical density of the chromagenic reaction product is then measured, whereby the optical density is directly proportional to the amount of 6-MMP produced by enzyme-catalyzed TPMT methylation.

One unit of TPMT activity is defined as the amount of enzyme needed to catalyze formation of 1 nmole of 6-MMP in 60 minutes at 37° C., as judged by radiometric incorporation of $^{14}$C-methyl-SAM into 6-mercaptopurine. It has been shown that the TPMT activity in red blood cells (RBCs) ranges from 4.6 to 14.2 units/ml of packed RBCs. The TPMT phenotype is assigned on the basis of TPMT activity in erythrocytes. Patients who have <5.0 U/ml are considered TPMT deficient, while those who have 5–10 U/ml are considered heterozygous, and those who have >10 U/ml are considered homozygous wild-type (Weinshilboum and Sladek, 1980). Using the non-isotopic ELISA assay of this invention, based upon binding of anti-6MMP antibody to in vitro methylated 6-mercaptopurine-carrier protein bound to plastic wells, 4.6 to 14.2 radiometric TPMT Units corresponds to about 0.3 to 1.0 $A_{450}$nm Units.

The following examples are offered to illustrate but not limit the invention. Thus, it is presented with the understanding that various formulation modifications as well as method of delivery modifications may be made and still are within the spirit of the invention.

EXAMPLE 1

Preparation of Non-Isotopic TPMT Immunoassays

Not only is there no available non-isotopic immunoassay for TPMT, there is also at present no commercial supplier of TPMT, which can be used as a positive control for enzyme assays. Accordingly, (A) considerable effort was expended to clone and express the human TPMT enzyme in *E.coli*; and to partially purify, characterize, and optimize recombinant hTPMT; (B) High titer rabbit antibodies to 6-MMP were produced; and purified anti-6-MMP IgG was demonstrated to bind specifically to 6-MMP—but not to unmethylated 6-mercaptopurine.

A. Cloning, Expression, and Purification of Human TPMT

As a first step towards developing a rapid, non-isotopic assay for TPMT in red blood cells, adequate quantities of the human TPMT enzyme for control assays were needed. Therefore, the TPMT enzyme from human lymphocyte DNA was cloned and over-expressed, based upon the sequence data of Szumlanski et al. (1996).

Briefly, the cloning strategy was to insert the PCR-amplified TPMT gene fused in-frame to the N-terminus of the LacZ gene in the plasmid cloning vector pGEM-3Zf(+) (Promega, Madison, Wis.). A 738 b.p. DNA fragment containing the human TPMT gene was PCR-amplified, digested using BamHI and HindIII, and then inserted between the BamHI site and the HindIII site of pGEM-3Zf(+).

1. PCR Amplification of the Human TPMT Gene

Amplification of a 738 b.p. DNA fragment containing the human TPMT coding sequence was carried out using "tailed" primers which contained ends suitable for insertion into the BamHI and HindlIII sites of pGEM-3Zf(+).

```
Forward primer:  5' TACGCCAAGCTTAATGGATGGTACAAGAACTTCACTTG 3'   (SEQ ID NO:1)
Reverse primer:  5' GGTACCCGGGGATCCTTACTTTTCTGTAAGTAGACATAAC 3'  (SEQ ID NO:2)
```

These primers contained a gene-specific sequence of 25 b.p. (underlined), but also carried a non-TPMT cloning sequence (a "tail") at their 5' end (13 and 15 b.p., respectively, for the Forward and Reverse primer). These cloning sites were used to insert the PCR product in-frame into the cloning vector after cutting with the appropriate restriction endonucleases, BamHI+HindIII. This cloning strategy resulted in a forced orientation of the inserted TPMT PCR product into the pGEM-3Zf(+) cloning vector, so that TPMT was under LacZ transcriptional control and thereby inducible using IPTG.

2. Construction of a Recombinant Plasmid Containing the Human TPMT Gene

The PCR product containing the amplified human TPMT coding sequence as a 738 b.p. DNA fragment was cut using BamHI and HindIII endonucleases and then inserted into a similarly cut pGEM-3Zf(+) vector (Promega, Madison, Wis.), as shown below.

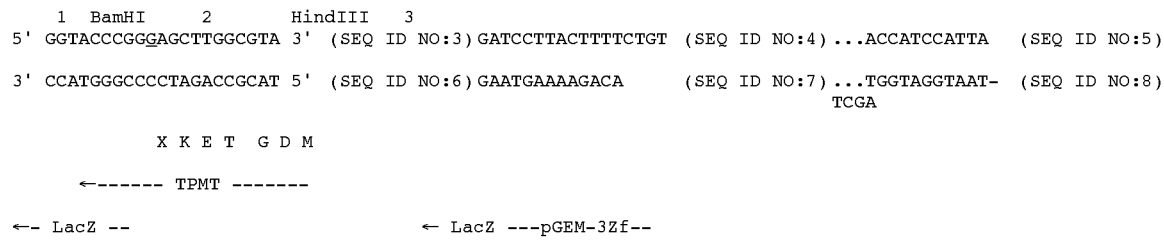

Insertion of PCR-amplified TPMT Gene into pGEM-3Zf(+). The PCR-amplified Human TPMT gene, containing appropriate BamHI and HindIII cohesive ends, was cut using BamHI and HindIII endonucleases removing pieces #1 and #3. The resulting piece #2 has cohesive ends for insertion into pGEM-3Zf(+) vector cut under the same conditions. Ligation of fragment #2 into BamHI+HindIII digested pGEM-3Zf(+) resulted in a plasmid in which the human TPMT gene is fused in-frame to the first 13 codons of LacZ.

The ligated [pGEM-3Zf(+) vector +TPMT insert] DNA reaction product was then transformed into JM109 competent cells, followed by selection for ampicillin-resistant colonies. Four Amp$^R$ colonies were tested for (a) presence of the human TPMT gene insert by PCR-amplification; (b)

restriction enzyme fingerprinting. One plasmid, named pTPMT, was selected for further study.

3. Overexpression of Recombinant Human TPMT using *E.coli* JM109 (pTPMT) Cells

Plated *E.coli* JM109 (pTPMT) colonies carrying the cloned human TPMT gene were grown for 6 hours in 100 ml of Terrific Broth (TB). 10 liters of TB were supplemented with 50 µg/ml of Ampicillin, inoculated with 100 ml of the 6 hour culture and allowed to grow at 37° C. with vigorous shaking to an A600 of 0–6 (~5–6 hours). The log phase culture was induced with 100 mM IPTG to a final concentration of 0.4 mM. The culture was incubated overnight at 37° C. with vigorous shaking. The cells were harvested by centrifugation and stored frozen. at −20° C.

4. Partial Purification of Recombinant Human TPMT Enzyme

Figure 2:
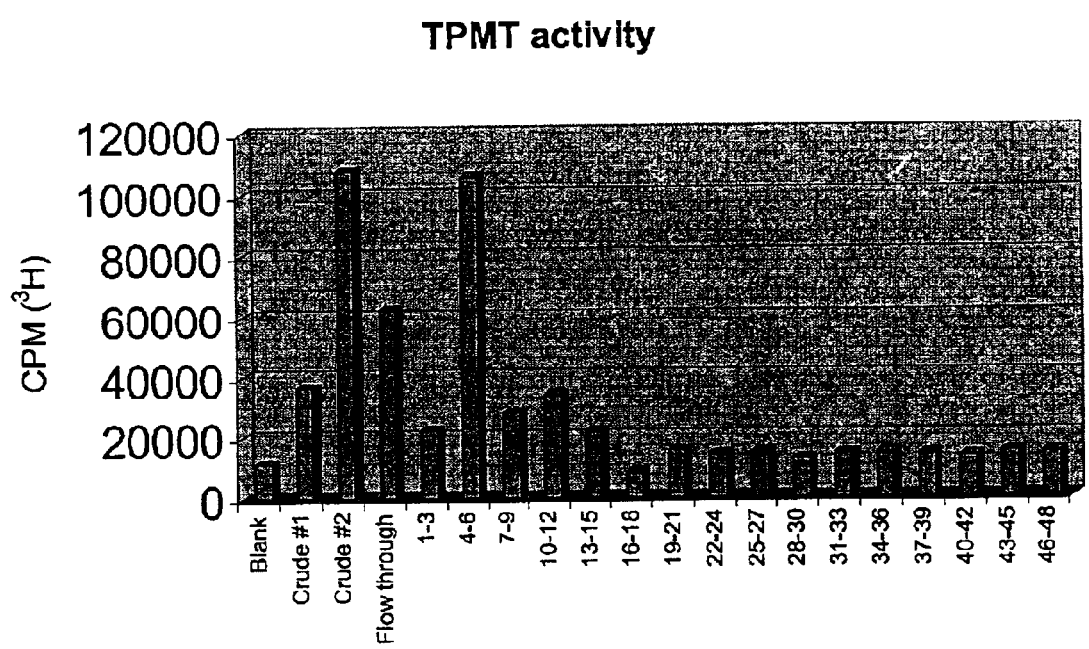
FIG. 2 is a radiometric assay of recombinant human TPMT enzyme activity in Q-sepharose chromatography fractions. 3 $\mu$l of crude extract or Q-sepharose column fraction from IPTG-induced E.coli JM109 (pTPMT) cells was incubated for 30 minutes at 37° C. in a 300 $\mu$l reaction containing (1 mM $KPO_4$, 30 mM Tris-Cl, pH 8.0, 1 mM EDTA, 10% DMSO, ~2 $\mu$M $^3$H-methyl-SAM, and 1% (vol/vol) 2-bromothiophenol substrate), followed by the addition of 110 $\mu$l of 0.5M Na Borate, pH 10, and organic extraction into 0.7 ml toluene. Liquid scintillation counting was carried out in toluene fluor+10% ethanol. TPMT enzyme activity is expressed as $^3$H-methyl c.p.m. incorporated into the organic layer. The TPMT enzyme eluted from the Q-Sepharose column between fractions #4–12, with some of the activity in the flowthrough.

Thawed cells (~15g) were sonicated in (20 mM Tris-Cl, pH 7.5, 1 mM EDTA, 50 mM KCl, 10 mM β-mercaptoethanol) and centrifuged (8000 g for 15 minutes). The supernatant was loaded onto a Q-Sepharose column (Pharmacia, Piscataway, N.J.). The column was eluted with a 200 ml linear gradient from 0 to 0.8 M KCl in (20 mM Tris-HCl, pH 7.5, 1 mM EDTA, 5% w/v glycerol. Fractions (~4 ml) were collected and tested for TPMT enzyme activity using 2-Bromothiophenol as a substrate (Woodson et al., 1983). Results from radiometric assays for TPMT activity from *E.coli* JM109(pTPMT) after fractionation on Q-Sepharose are shown in FIG. 2.

The Q-Sepharose fractions containing TPMT activity (fractions #4–12) were precipitated using 70% ammonium sulfate. The precipitate was re-suspended in (20 mM Tris-Cl, pH 7.5, 1 mM EDTA, 0.1 M KCl, 5% glycerol), dialyzed briefly against the same buffer, and loaded onto a Hydroxylapatite (BioRad HTP) column. The concentrated Q-Sepharose enzyme fraction did not stick to the HTP column; but a considerable amount of yellow-colored protein was removed. Further enzyme purification seemed to adversely affect enzyme activity.

5. Temperature Optimum and Stability of Recombinant TPMT

The optimal reaction temperature for the hTPMT enzyme is 37° C. TPMT did not tolerate temperatures above ~37° C., but the enzyme was nearly as active at 23° C. The relatively high activity of TPMT at ambient temperature facilitates immunoassays using anti-6-MMP antibody. After a storage of 2 and 5 months at −20° C., no change in TPMT enzyme activity was observed.

B. Immunochemical (Non-Isotopic) Detection of TPMT

Having produced adequate quantities of stable, partially purified recombinant TPMT enzyme for test assays, the next step was to produce suitable anti-6-MMP antibodies. These antibodies were used to immunochemically detect 6-MMP, the reaction product of TPMT-catalyzed methylation of 6-mercaptopurine.

1. Production of Antibodies to 6-MMP

Antibodies to the ribonucleoside of 6-MMP were prepared using an adaptation of the periodate oxidation method of Erlanger and Beiser (1964), as modified by Stollar (1980). Briefly, 1 mmole 6-methylmercaptopurine riboside was oxidized to the dialdehyde using sodium m-periodate. The resulting the free amino groups of lysine. The Schiff's bases were stabilized by reduction with sodium cyanoborohydride. The resulting hemocyanin:6-MMP riboside conjugate was dialyzed extensively against 30 mM Sodium bicarbonate buffer and stored at 4° C. Antibodies were produced at Southern Biotechnology, Birmingham, Ala., using 1 mg of hemocyanin:6-MMP riboside conjugate for initial injection and 0.5 mg for subsequent boosts. Serum samples were collected after every booster injection and stored frozen at −20° C.

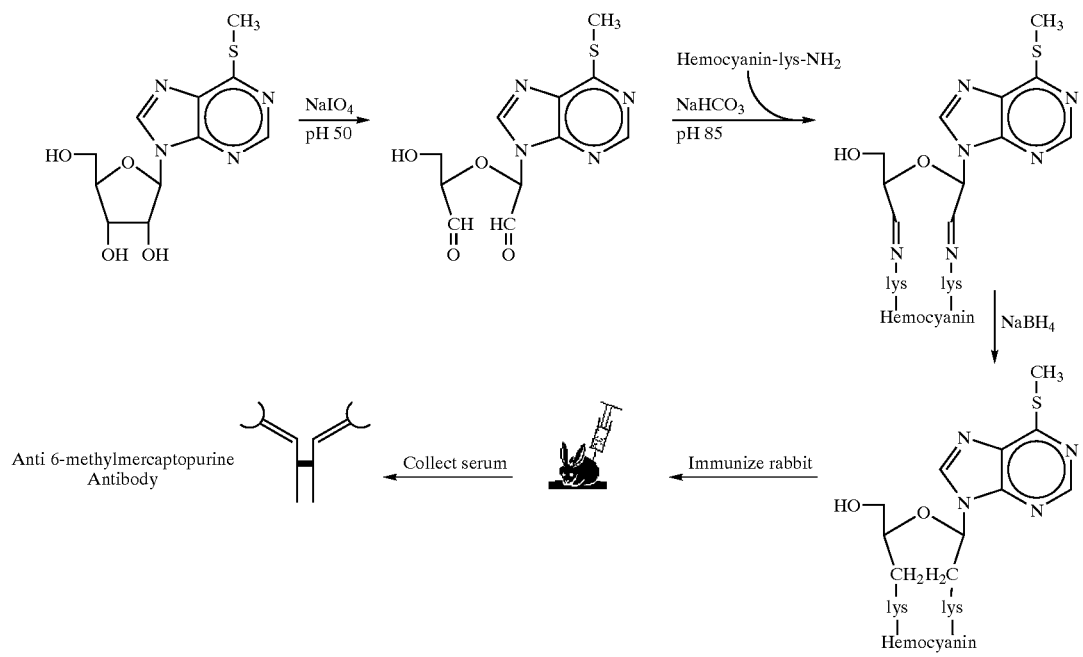

Schematic Diagram of Procedure for Preparation of Rabbit Anti-6-MMP Antibodies

2. Purification of Rabbit-Anti-6-MMP IgG using Protein A Affinity Chromatography Rabbit anti-6-MMP IgG was purified from immune serum using a Protein A affinity column (Immunopure Plus Immobilized Protein A Kit; Pierce Chemical Co., Rockford, Ill.)

according to the manufacturer's instructions. The eluted anti-6-MMP IgG fractions were monitored by absorbance at 280 nm. Fractions containing the highest amount of IgG were pooled together and dialyzed against PBS. The purified anti-6-MMP IgG was stored at 4° C.

3. Development of an Enzyme Linked Immunosorbent Assay (ELISA)

The reactivity of anti-6-MMP IgG and its cross-reactivity, if any, to 6-MP were tested using ELISA format. Since both 6-MP (TPMT substrate) and 6-MMP (TPMT reaction product) are small molecules, they did not bind significantly to the plastic plates. Therefore, both molecules were linked to BSA using similar periodate oxidation chemistry to that shown in the schematic above. Immulon 1B Davidstrip assemblies (Dynex Technologies Inc. Chantilly, Va.) were initially coated with BSA:6-MP or BSA:6-MMP by incubating each well with 100 μl of 1 μg/ml or 10 μg/ml conjugates. ELISA strips were left at room temperature overnight; and washed with PBS (10 mM sodium Phosphate, pH 7.5, 150 mM NaCl) to remove unbound antigen. Strips were stored in a sealed bag at 4° C. for up to 3 months.

When necessary, strips were removed and blocked with 100 μl PBS containing 1% nonfat milk as a blocking reagent, followed by incubation at room temperature (RT) for 30 minutes. The wells were emptied and 100 μl of rabbit anti-6-MMP IgG diluted to 10, 5, or 1 μg/ml in PBS was added to wells. After incubating for 20 minutes at RT the antibody solution was discarded and the wells received 100 μl of horseradish peroxidase labeled Protein A/G conjugate (HRP-labeled goat anti-rabbit IgG; Pierce Chemical Co., Rockford, Ill.) diluted 1:10,000 in PBS. After incubating for 20 min at RT the wells were washed four times with PBS-T (Phosphate Buffered Saline+0.1% Tween-20) and one time with PBS. The wells were developed with 100 μl of TMB substrate (Kirkegaard and Perry Laboratories, Gaithersberg, Md.). The color reaction was stopped after 10 minutes by the addition of 100 μl of 0.18 M sulfuric acid per well. Absorbance was read on an Opsys MR ELISA plate reader (Dynex) at 450 nm. Controls included wells with buffer alone and wells without antigens.

The anti-6-MMP IgG reacted with BSA-6MMP conjugate readily at all concentrations tested. The best signal (>2.0 OD units) was at 5 or 10 μg/ml, with no reaction toward unconjugated BSA alone. However, significant binding to 6-MP was seen, which was not surprising. In order to remove these cross-reacting antibodies to 6-MP, an affinity column with 6-MP coupled to Bio-Gel P-30 was prepared. Protein A purified antibody preparation was passed over this column to adsorb the 6-MP reacting antibodies and was tested again in ELISA. This purified anti-6-MMP IgG preparation did not show any activity to unmethylated 6-MP and reacted very specifically with 6-MMP, indicating that the 6-MP cross-reacting antibody was completely removed.

In any ELISA development, it is important to test the specificity and sensitivity of the detection antibody. Once the purified anti-6-MMP IgG was determined to be specific for 6-MMP, the next step was to check if it was sensitive enough to detect the in vitro methylated 6-MMP reaction product in a TPMT enzyme-catalyzed reaction.

4. ELISA Immunoassay for TPMT using Purified Anti-6-MMP IgG

In order to determine whether TPMT enzyme could methylate 6-MP bound to BSA in reaction wells of a plastic ELISA plate, and if the anti-6-MMP antibody could detect the methylated 6-MMP reaction product, the following assay format was developed:

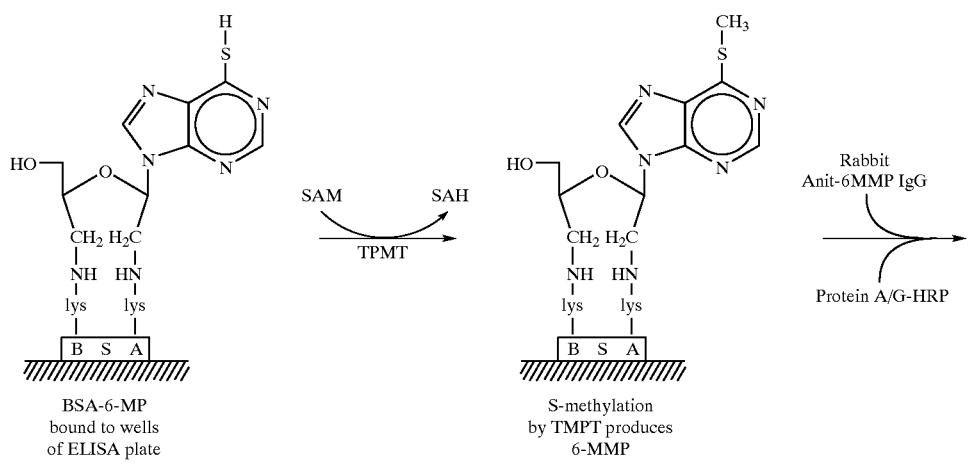

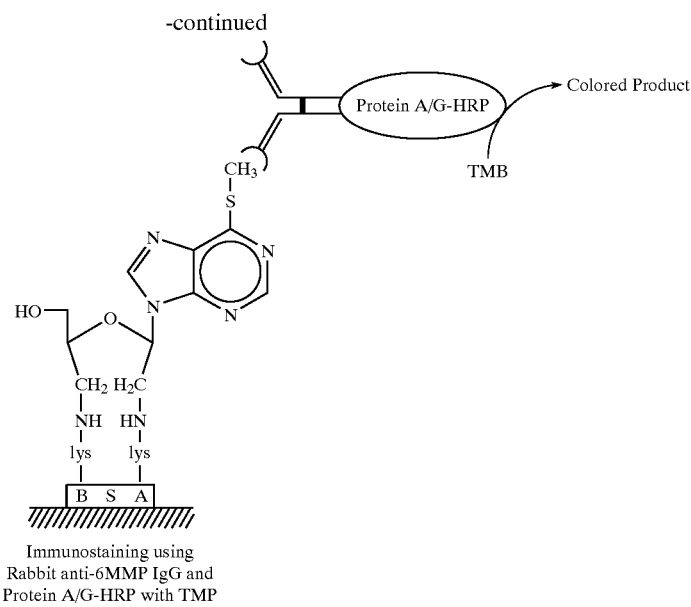

Immunostaining using
Rabbit anti-6MMP IgG and
Protein A/G-HRP with TMP

Schematic Representation of ELISA Assay for TPMT. Substrate BSA-6-mercaptopurine conjugate is coated onto the wells of plastic ELISA plates. In the presence of S-Adenosylmethionine (SAM), TPMT catalyses S-methylation of 6-MP to 6-methylmercaptopurine (6-MMP). Rabbit anti-6-MMP IgG binds to the covalently bound 6-MMP reaction product; and Protein A-Horseradish peroxidase (HRP) conjugate then binds to the rabbit IgG. Blue color develops in the presence of the HRP substrate, Tetramethylbenzidine. After acidification, the color changes to yellow; and the optical density at 450 nm is directly proportional to the amount of 6-MMP produced by enzyme-catalyzed TPMT methylation.

The wells of 'Immulon B' ELISA strips were coated with various concentrations of BSA-6MP conjugate and blocked as described above. After blocking solution was removed, the wells received 100 μl of Methylation Reaction Mix consisting of 1 mM Potassium Phosphate, 30 mM Tris-HCl, pH 8.0, lmM EDTA, 100 μM SAM and 1–4 μl of TPMT enzyme (~6 units/μl). As a control, the wells received 100 μl of same reaction mix except no Mtase enzyme.

The wells were incubated at 37° C. for 30 minutes and were developed as described before. Absorbance was read on an Opsys MR ELISA plate reader (Dynex) at 450 nm. In this ELISA assay format, TPMT enzyme activity is detected as the amount of 6-MMP formed in situ: substrate 6-mercaptopurine is covalently bound to BSA which coats the wells of the plastic ELISA plate. Since anti-6-MMP IgG binds specifically to the methylated reaction product, 6-MMP, it is possible to measure TPMT activity using horseradish peroxidase (HRP) labeled Protein A (or HRP-conjugated goat anti-rabbit IgG). Upon development using tetramethylbenzidine as a peroxidase substrate, the optical signal at 450 nm is directly proportional to the amount of 6-MMP formed in the TPMT-catalyzed reaction.

TABLE 1

Detection of TPMT Enzyme in ELISA

| Concentration of BSA:6-MP | Absorbance at 450 nm | TPMT Enzyme activity |
|---|---|---|
| 1 mg/ml | 2.561 | ++ |
| 100 μg/ml | 2.440 | ++ |
| 10 μg/ml | 2.228 | ++ |
| 0 μg/ml | 0.053 | − |

The ELISA immunoassay for detection of TPMT enzyme activity using anti-6-MMP IgG worked extremely well. In the presence of S-adenosylmethionine (SAM), recombinant hTPMT enzyme methylated BSA-6MP conjugate which had been adsorbed to the plastic wells of an ELISA plate. Results from one such TPMT immunoassay are shown in Table 1 above. Using as little as 10 μg/ml BSA:6-MP conjugate to coat plastic ELISA wells, a signal of <2 $A_{450}$ nm Units was observed after in vitro TPMT methylation, against a background signal of ~0.05 $A_{450}$ Units.

5. Summary of Preliminary Results

The study above demonstrates the successful cloning, overexpression, and partial purification of human thiopurine methyltransferase, so that sufficient quantities of enzyme are available for TPMT immunoassays. Secondly, high titer rabbit anti-6-MMP antibodies have been prepared. Anti-6-MMP IgG fractions have been purified by a combination of Protein A Sepharose and affinity chromatography, using a 6-MP resin. These purified antibodies react specifically with 6-MMP, but not with 6-mercaptopurine. Finally, the feasibility of ELISA-based immunoenzymatic detection of TPMT has been demonstrated, using partially purified recombinant TPMT enzyme, as shown in Table 1.

EXAMPLE 2

Rapid Immunimigration (RIM) Cassette Assay for TPMT

As noted above, the Rapid Immunomigration (RIM) Cassettes of this invention are inexpensive, and allow for rapid, homogenous TPMT immunoassays. A purple band in the lower mobility position of the cassette signifies the presence of wild-type levels of TPMT, while a light purple or absent band indicates partial or complete TPMT deficiency.

1. Preparation of Red Blood Cell Lysates

Red blood cell extracts are prepared by a modification of the method of Weinshilboum et al (1978). About ~1 ml of blood is drawn, then the erythrocytes are pelleted by 5 minute centrifugation at 3000 g. The pelleted cells (~$10^8$) are resuspended in 0.5 ml of PBS. 2 ml of cold distilled water is added to achieve hypotonic lysis, followed by brief centrifugation. The supernatant (red blood cell lysate) is stored on ice prior to TPMT enzyme assays. For long term storage the lysate can be stored at −85° C. without loss in enzyme activity.

2. Preparation and Purification of Anti-6-MMP Antibody

Rabbit antibody to the riboside of 6-methylmercaptopurine (6-MMP) is prepared as already described. Immune serum is purified on Protein A Sepharose, followed by affinity adsorption on 6-MP Biogel. Purified anti-6-MMP immunoglobin (IgG) is dialyzed against PBS containing 0.1% sodium azide and stored at 4° C. This IgG fraction has previously been shown to be specific for methylated 6-MMP at concentrations as low as 1 µg/ml (~5 nanomolar IgG), but does not bind to unmethylated 6-mercaptopurine.

3. Preparation of Colloidal Gold-labeled Anti-6-MMP IgG

Anti-6-MMP IgG is labeled with colloidal gold using the procedure of Lin and Langenberg (1983). Gold-IgG complexes are centrifuged at 10,000 rpm for 60 minutes in an SS-34 rotor at 4° C., and the soft pellet is resuspended in 0.1 M Potassium phosphate, pH 7.4, 0.05% Sodium azide, containing 4% polyvinylpyrrolidone (PVP; m.w. ~10,000) and 0.4 mg/ml polyethylene glycol (PEG; m.w. ~12,000). Large aggregates are removed by 5 min. centrifugation at 10,000 r.p.m.

4. Preparation of Substrates for TPMT Immunocassettes

A variety of aromatic thiols have been shown to be good substrates for TPMT (Ames et al, 1986; Woodson et al, 1983). In particular, 6-mercaptopurine riboside is a relatively good substrate for human TPMT (Deininger et al., 1994, Table 1). However, it is necessary to be able to trap the reaction product of TPMT-catalyzed methylation of 6-mercaptopurine riboside using Rapid Immunomigration cassettes containing anti-6-MMP antibody. In order to do so, a "bridging" substrate is prepared, which is suitable for immunoprecipitation, i.e., a molecule which contains 6-MP riboside and a biotin moiety for capture using immobilized avidin.

Two different substrates were prepared. (a) Biotinylated BSA-6MP conjugate, as already described, except that the BSA will be chemically biotinylated using PEO Biotin maleimide (Pierce Chemical Co., Rockford, Ill.). In the resulting protein conjugate, the cysteines of BSA are coupled to biotin, and the lysines are derivatized with 6-mercaptopurine riboside. This derivatized protein molecule is therefore both a substrate for TPMT (covalently attached 6-MP residues) and can be trapped by gold-labeled anti-6-MMP antibody.

Secondly (b), a lower molecular weight biotinylated TPMT substrate was synthesized by reaction of periodate oxidized 6-mercaptopurine riboside with Biocytin Hydrazide (Pierce Chemical Co., Rockford, Ill.). The resulting 6-MP-biocytin acyl hydrazide is a much smaller "bridging" molecule than BSA, ~20 Angstrom spacer arm separates the biotin moiety from the 6-MP. This smaller TPMT substrate is expected to diffuse faster and give more sensitive immunoprecipitation reactions with both avidin and gold-labeled anti-6-MMP antibody.

5. Design of Immunocassettes for Detection of 6-MMP

Immunochromatography, also known as Rapid Immunomigration (RIM), is one of the fastest and most practical techniques to detect antibody-antigen interactions. In the most common format for this method, an antibody specific to a given antigen is fixed to colloidal gold molecules, which is dried as a stripe on chromatography paper (usually a nitrocellulose or PVDF) strip encased in a plastic holder or 'immunocassette', as shown in FIG. 1.

Additional "capture" molecule such as avidin and Protein A are also dried onto the paper. Gold-labeled antibodies and/or avidin bind to haptens which are introduced into the immunocassette.

A drop (~10 to 12 µl) of the test substance is dropped through a window in the holder onto the paper. In positive (immunoreactive) samples, an antigen-antibody-gold particle complex is formed. This complex migrates along the paper and is eventually trapped by a ligand that is coated to the paper at a defined location. This trapping ligand can be Protein A, an antibody specific for the primary antibody, and/or avidin, which is capable of trapping the biotinylated gold-antibody-antigen complexes. Trapping of the immunoprecipitate complex allows the visualization of the particles in a transparent window in the RIM apparatus.

6. Protocol for the Detection of TPMT Enzyme Activity Using Immunocassettes

Biotinylated BSA-6MP (1 to 10 µg/ml) or Biocytin-6-MP substrates are incubated with 5 to 10 U of partially purified TPMT enzyme (6 units/µl) or 2 to 10 µl of red blood cell lysate in a TPMT methylation reaction mix containing: (1mM Potassium Phosphate, 30 mM Tris-HCl, pH 8.0, 1 mM EDTA, 100 µM SAM) in a 50 µl reaction volume at 37° C. After 10 to 30 minutes, 10 µl of this reaction mixture is squirted into the sample window of the anti-6-MMP immunocassette. When the sample is completely absorbed, 4 drops of saline developing solution (~200, µl) is added and observed for the purple sample band. As a negative control, BSA-6-MP conjugate or Biocytin-6-MP substrates are incubated in the same way, but without the addition of TPMT enzyme.

7. Determination of TPMT Enzyme Activity: Reading the Cassettes

Using such immunocassettes, a visible purple color appears in the window when immunoreactive molecules are present in the sample (i.e., TPMT+/+); and the intensity of the color allows semi-quantitation (i.e., dark purple= TPMT+/+ versus light purple=TPMT+/−). On the other hand, if no methylated immunoreactive molecules are present, then the immunocassette remains colorless. An internal control is included, which serves to allow the user to validate that the cassette reagents (Au-labeled antibody, avidin, Protein A) are working as expected. The migration position of the internal control is arranged to be slightly different from that of the experimental sample.

8. Manufacture and Optimization: Building the TPMT Immunocassettes

It is expected that anti-6-MMP immunocassette optimization and standardization will provide TPMT detection kits able to determine the presence or absence of wild-type TPMT enzyme from blood samples in as little as 30 minutes for a low cost. The value of the TPMT immunocassette assay is its low cost, speed, and ability to identify the ~90% of TPMT-proficient patients to whom thiopurine drugs can be safely given. In cases where partial or complete TPMT deficiency is observed, a more accurate ELISA test may be performed.

EXAMPLE 3

Development of a Quantitative ELISA Assay for Red Blood Cell TPMT

As noted above, in certain cases, especially those in which TPMT levels are low or absent using rapid immunocassette assays, it may be important to determine the levels of TPMT activity more precisely. A quantitative TPMT ELISA assay would help a physician in deciding the correct dosage of thiopurine drugs which should be given to patients.

1. Preparation of BSA-6MP Substrate and Coating of Plastic ELISA Plates

BSA-6MP substrate for ELISA assays is prepared as already described above. Wells of plastic ELISA strips are coated at a concentration of 50–100 µg/ml 6MP-BSA (Table 1). This substrate concentration is more than sufficient for immuno-chemical detection of TPMT using rabbit anti-6MMP IgG and peroxidase conjugated ProteinA/G. Coated plates are stored in sealed plastic bags at 4° C. prior to use.

2. Development of Quantitative ELISA for TPMT

Quantitative ELISA tests are performed using 1 to 20 Units of purified TPMT enzyme added per well as described above. Absorbance at 450 nm is measured and plotted against units/ml of TPMT activity. The assay is repeated at least three times and mean values are used to generate standard plot. Absorbance is then corresponded to units of enzyme from the standard plot.

In conclusion, the present invention identifies three preferred embodiments for detecting TPMT:

1. A non-isotopic immunoassay for Thiopurine Methyltransferase (TPMT, in which the assay is carried out in a homogenous, Rapid Immunomigration Cassette (RIM) format.
2. A non-isotopic immunoassay for TPMT, in which the assay is carried out in a heterogenous, Enzyme Linked Immunosorbent (ELISA) assay format.
3. A non-isotopic immunoassay for TPMT, in which detection of the TPMT-catalyzed reaction product relies upon specific binding of antibody to 6-methylmercaptopurine (6MMP), either free or bound to a carrier molecule or solid support.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence, which is effective to meet the objectives there intended, unless the context specifically indicates to the contrary.

All articles cited herein and in the following list are hereby expressly incorporated in their entirety by reference.

Citations

1. Ames M M, Selassie C D, Woodson L C, Van Loon J A, Hansch C, and Weinshilboum R M (1986) "Thiopurine Methyltransferase: Structure-Activity Relationships for Benzoic Acid Inhibitors and Thiophenol Substrates." J. Med. Chem. 29: 354–358.
2. Boulieu R and Lenoir A (1995) "Determination of thiopurine nucleotides in human lung tissue by high-performance liquid chromatography." J. Chromatography 665: 213–216.
3. Cosi V, Lombardi M, Erbetta A, and Piccolo G (1993) "Azathioprine as a single immunosuppressive drug in the treatment of myasthenia gravis." Acta Neurol. 15: 123–31.
4. Deininger M, Szumlanski C L, Otterness D M, Van Loon J, Ferber W, and Weinshilboum R M (1994) "Purine Substrates for Human TPMT." Biochem. Pharmacol. 48: 2135–2138.
5. Elion G B (1989) "The purine pathway to chemotherapy." Science 244: 41–47.
6. Erlanger B F and Beiser S M (1964) "Antibodies to methylated bases in nucleic acids." Proc. Nat. Acad. Sciences USA 52: 68–71.
7. Evans W E and Krynetski E Y (1999) "Identification of two novel mutant alleles of human thiopurine methyltransferase, and diagnostic uses thereof." U.S. Pat. No. 5,856,095.
8. Evans W E, Horner M, Chu Y Q, Kalwinsky D, and Roberts W M (1991) "Altered mercaptopurine metabolism, toxic effects, and dosage requirement in a thiopurine methyltransferase-deficient child with acute lymphocytic leukemia." J. Pediatrics 119: 985–989.
9. Glied M and Rico M J (1999) "Treatment of autoimmune blistering diseases." Dermatol.Clin. 17: 431–440.
10. Gummert J F, Schutz E, Oellerich M, Mohr F W, and Dalichau H (1995) "Monitoring TPMT in heart transplant recipients under immunosuppressive therapy with azathioprine." Artificial Organs 19: 918–920.
11. Heller M J (2000) "Microelectronic Array Devices for DNA Diagnostic, Pharmacogenetic, and Nanofabrication Applications." NIH Conference on "Nanoscience and Nano-technology: Shaping Biomedical Research," Bethesda, Md., Jun. 25–26, 2000.
12. Iyer L and Ratain MJ (1998) "Pharmacogenetics and cancer chemotherapy." Eur. J. Cancer 34: 1493–99.
13. Jackson A P, Hall A G, and McClelland J (1997) "Thiopurine methyltransferase levels should be measured before commencing patients on azathioprine." Brit. J. Dermatol. 136: 133–134.
14. Johnson P J, McFarlane I G, and Williams R (1995) "Azathioprine for long-term maintenance of remission in autoimmune hepatitis." New Eng. J. Med. 333: 958–963.
15. Kroplin T, Weyer N, Gusche S, and Iven H (1998) "Thiopurine S-methyltransferase activity in human erythrocytes: a new HPLC method using 6-thioguanine as substrate." Eur. J. Clin. Pharmacol. 54: 265–271.
16. Krynetski E Y and Evans W E (1998) "Pharmacogenetics of cancer therapy: getting personal." Am. J. Human Genetics 63: 11–16.
17. Krynetski E Y, Schuetz J, Galpin A, Pui C-H, Relling M V, and Evans W E (1995) "A single point mutation leading to loss of catalytic activity in human thiopurine methyltransferase." Proc. Nat. Acad. Sciences USA 92: 949–953.
18. Lennard L (1998) "Clinical implications of thiopurine methyltransferase—optimization of drug dosage and potential drug interactions." Ther. Drug Monitoring 20: 527–531.
19. Lennard L (1999) "Therapeutic drug monitoring of antimetabolic cytotoxic drugs." British J. Clinical Pharmacol. 47: 131–143.
20. Lennard L and Lilleyman J S (1987) "Are children with lymphoblastic leukaemia given enough 6-mercaptopurine?" Lancet 2: 785–787.
21. Lennard L, Van Loon J A, Lilleyman J S, and Weinshilboum R M (1987) "Thiopurine pharmacogenetics in leukemia: Correlation of erythrocyte TPMT activity and 6-thioguanine nucleotide concentrations." Clin. Pharmacol. Therap. 41: 18–24.
22. Lennard L, Gibson B E, and Lilleyman J S (1993) "Congenital thiopurine methyl-transferase deficiency and 6-mercaptopurine toxicity during treatment for acute lymphoblastic leukemia." Arch. Diseases of Children 69: 577–579.
23. Lennard L and Lilleyman J S (1996) "Individualizing therapy with 6-mercaptopurine and 6-thioguanine related to the thiopurine Mtase genetic polymorphism." Therap. Drug Monitoring 18: 328–334.
24. Lin N S and Langenberg W G (1983) "Immunohistochemical Localization of Barley Stripe Mosaic Virions in Infected Wheat Cells." J. Ultrastructure Res. 84: 16–23.
25. Lopez O J and Nelson R M (1998) "DNA Mtase Genotyping." U.S. patent application Ser. No. 98/17859.
26. Meyer U A, Zanger U M, Grant D, and Blum M (1990) "Genetic Polymorphisms of Drug Metabolism." Advances in Drug Research 19: 197–241.
27. Micheli V, Jacomelli G, Fioravanti A, Morozzi G, Marcolongo R, and Pompucci G (1997) "Thiopurine methyltransferase activity in the erythrocytes of adults and children and HPLC linked assay." Clin. Chimica Acta 259: 161–168.
28. Pearson D C, May G R, Fick G H, and Sutherland L R (1995) "Azathioprine and 6-mercaptopurine in Crohn disease." Ann. Intern. Med. 123: 132–142.
29. Sandborn W J, Van 0 E C, Zins B J, Tremaine W J, Mays D C, and Lipsky J J (1995) "An Intravenous loading dose of azathioprine decreases the time to response in patients with Crohn's disease." Gastroenterology 109: 1808–1817.
30. Schutz E, Gummert J, Mohr F, and Oellerich M (1993) "Azathioprine-induced myelo-suppression in a TPMT deficient heart transplant recipient." Lancet 341: 436.
31. Schutz E, Gummert J, Armstrong V W, Mohr F W, and Oellerich M (1996) "Azathioprine pharmacogenetics: the relationship between 6-thioguanine nucleotides and thiopurine Mtase in patients after heart and kidney transplantation." Eur. J. Clin. Chem. Clin. Biochem. 34: 199–205.
32. Spire-Vayron de la Moureyre C, Debuysere H, Mastain B, Vinner E, Marez D, Lo Guidice J M, Chevalier D, Brique S, Motte K, Colombel J F, Turck D, Noel C, Flipo R M, Pol A, Lhermitte M, Lafitte J J, Libersa C, and Broly F (1998) "Genotypic and phenotypic analysis of the polymorphic thiopurine S-methyltransferase gene in a European population." British J. Pharmacol. 125: 879–887.
33. Stollar B D (1980) "The Experimental Induction of Antibodies to Nucleic Acids." Meth Enzymol. 70: 70–85.
34. Szumlanski C, Otterness D, Her C, Lee D, Brandriff B, Kelsell D, Spurr N, Lennard L, Wieben E, and Weinshilboum R M (1996) "Thiopurine Mtase Pharmacogenetics: Human Gene Cloning and Characterization of a Common Polymorphism." DNA & Cell Biol. 15: 17–30.
35. Tan B B, Lear J T, Gawkrodger D J, and English J S (1997) "Azathioprine in dermatology: a survey of current practice in the U.K." 136: 351–355.
36. University of Rochester Medical Center (1999) "Dermatology Laboratory Tests: Thiopurine Methyltransferase (TPMT), E C 2.1.1.67, Red Blood Cells."
37. Weinshilboum R M (1984) "Human pharmacogenetics of methyl conjugation." Pharmacol.Ther. 43: 77–90.
38. Weinshilboum R M, Raymond F A, and Pazmino P A (1978) "Human erythrocyte thiopurine Mtase: Radiochemical microassay and biochemical properties." Clin. Chim. Acta 85: 323–333.
39. Weinshilboum R M, Otterness D M, and Szumlanski C L (1999) "Methylation Pharmacogenetics: Catechol O-Methyltransferase, Thiopurine Methyltrans-ferase, and Histamine N-Methyltransferase." Ann. Rev. Pharmacol. Toxicol. 39: 19–52.
40. Weinshilboum R M and Sladek S L (1980) "Thiopurine pharmacogenetics: monogenic inheritance of erythrocyte thiopurine Mtase activity." Am. J. Hum. Genet. 32: 651–662
41. Woodson L C, Ames M M, Selassi C D, Hansch C, and Weinshilboum R M (1983) "Thiopurine Mtase: Aromatic thiol substrates and inhibition by benzoic acid derivatives." Mol Pharmacol. 24:471–478.
42. Yates C R, Krynetski E Y, Loennechen T, Fessing M Y, Tai H-L, Pui C-H, Relling M V, and Evans W E (1997) "Molecular Diagnosis of Thiopurine S-Methyltransferase Deficiency: Genetic Basis for Azathioprine and Mercaptopurine Intolerance." Ann. Intern. Med. 126: 608–614.
43. Zhang X-D, Lotvall J, Skerfving S, and Welinder H (1997) "Antibody specificity to the chemical structures of organic acid anhydrides." Toxicology 118: 223–232.

What is claimed is:

1. A method of detecteing thiopurine methyltransferase (TPMT) comprising:

obtaining a biological sample from an individual;

assaying for the level of a TPMT-catalyzed reaction product, wherein said catalyzed reaction product is 6-methymercaptopurine (6-MMP) by contacting the biological sample with an antibody that binds 6-MMP to form a complex; detecting said complex; and correlate the detected complex to the amount of TPMT in said sample.

2. The method of claim 1 wherein the 6-MMP is free or bound to a carrier molecule or solid support.

3. The method of claim 1 wherein the antibody is a polyclonal antibody.

4. The method of claim 1 wherein the antibody is a monoclonal antibody.

5. The method of claim 1 wherein the biological sample is selected from the group consisting of blood, serum, and saliva.

6. The method of claim 1 wherein the detecting step further includes the substep of linking or incorporating a label into the antibody.

7. The method of claim 1 wherein the detecting step uses ELISA-based immunoenzymatic detection.

8. The method of claim 7 wherein the ELISA-based immunoenzymatic detection comprises the steps of: a) covalently binding substrate 6-mercaptopurine (6-MP) to a carrier protein to farm a conjugate; b) coating the wells of an ELISA plate with the conjugate; c) methylating the conjugate; and d) measuring the optical signal of the methylated conjugate.

9. The method of claim 8 wherein the optical signal is measured at about 450 nm.

* * * * *

UNITED STATES PATENT AND TRADEMARK OFFICE
CERTIFICATE OF CORRECTION

PATENT NO. : 6,946,258 B2 Page 1 of 1
DATED : September 20, 2005
INVENTOR(S) : Padhye et al.

It is certified that error appears in the above-identified patent and that said Letters Patent is hereby corrected as shown below:

Column 26,
Line 59, "farm" should read -- form --.

Signed and Sealed this

Thirteenth Day of December, 2005

JON W. DUDAS
*Director of the United States Patent and Trademark Office*

SEQUENCE LISTING

<160> NUMBER OF SEQ ID NOS: 8

<210> SEQ ID NO 1
<211> LENGTH: 38
<212> TYPE: DNA
<213> ORGANISM: Escherichia coli

<400> SEQUENCE: 1
tacgccaagc ttaatggatg gtacaagaac ttcacttg                              38

<210> SEQ ID NO 2
<211> LENGTH: 40
<212> TYPE: DNA
<213> ORGANISM: Escherichia coli

<400> SEQUENCE: 2
ggtacccggg gatccttact tttctgtaag tagacataac                            40

<210> SEQ ID NO 3
<211> LENGTH: 21
<212> TYPE: DNA
<213> ORGANISM: Escherichia coli -continued

```
<400> SEQUENCE: 3
ggtacccggg agcttggcgt a                                              21

<210> SEQ ID NO 4
<211> LENGTH: 17
<212> TYPE: DNA
<213> ORGANISM: Escherichia coli

<400> SEQUENCE: 4
gatccttact tttctgt                                                   17

<210> SEQ ID NO 5
<211> LENGTH: 11
<212> TYPE: DNA
<213> ORGANISM: Escherichia coli

<400> SEQUENCE: 5
accatccatt a                                                         11

<210> SEQ ID NO 6
<211> LENGTH: 21
<212> TYPE: DNA
<213> ORGANISM: Escherichia coli

<400> SEQUENCE: 6
ccatgggccc ctagaccgca t                                              21

<210> SEQ ID NO 7
<211> LENGTH: 13
<212> TYPE: DNA
<213> ORGANISM: Escherichia coli

<400> SEQUENCE: 7
gaatgaaaag aca                                                       13

<210> SEQ ID NO 8
<211> LENGTH: 15
<212> TYPE: DNA
<213> ORGANISM: Escherichia coli

<400> SEQUENCE: 8
tggtaggtaa ttcga                                                     15
```